(12) United States Patent
Isaacs et al.

(10) Patent No.: US 12,702,368 B2
(45) Date of Patent: Aug. 11, 2026

(54) IMAGING SYSTEM AND METHOD FOR IMAGE LOCALIZATION OF SURGICAL EFFECTORS USING C-ARM CHARACTERIZATION PARAMETERS

(71) Applicant: TrackX Technology, Inc., Hillsborough, NC (US)

(72) Inventors: Robert E. Isaacs, Chapel Hill, NC (US); Samuel Morris Johnston, Durham, NC (US); David A. Skwerer, Raleigh, NC (US); Randall Campbell, Hillsborough, NC (US)

(73) Assignee: TrackX Technology, Inc., Hillsborough, NC (US)

( * ) Notice: Subject to any disclaimer, the term of this patent is extended or adjusted under 35 U.S.C. 154(b) by 122 days.

(21) Appl. No.: 18/314,444

(22) Filed: May 9, 2023

(65) Prior Publication Data

US 2024/0374224 A1 Nov. 14, 2024

(51) Int. Cl.

| | |
|---|---|
| ***A61B 6/12*** | (2006.01) |
| ***A61B 6/00*** | (2024.01) |
| ***A61B 6/42*** | (2024.01) |
| ***A61B 6/46*** | (2024.01) |

(Continued)

(52) U.S. Cl.

CPC .............. *A61B 6/12* (2013.01); *A61B 6/4233* (2013.01); *A61B 6/4441* (2013.01); *A61B 6/463* (2013.01); *A61B 6/50* (2013.01); *A61B 6/5205* (2013.01); *A61B 6/547* (2013.01); *A61B 6/563* (2013.01); *A61B 2090/3966* (2016.02)

(58) Field of Classification Search

CPC ...... A61B 2090/376; A61B 2090/3966; A61B 6/12; A61B 6/4233; A61B 6/4441; A61B 6/463; A61B 6/50; A61B 6/5205; A61B 6/547; A61B 6/563

See application file for complete search history.

(56) References Cited

U.S. PATENT DOCUMENTS

| | | | |
|---|---|---|---|
| 7,097,357 | B2 | 8/2006 | Johnson et al. |
| 10,441,367 | B2 | 10/2019 | Isaacs et al. |
| 10,736,601 | B2 | 8/2020 | Kopperdahl et al. |

(Continued)

OTHER PUBLICATIONS

International Search Report and Written Opinion from corresponding PCT/US2024/028479, mailed Oct. 30, 2024. (13 pages).

*Primary Examiner* — Michael T Rozanski

(74) *Attorney, Agent, or Firm* — Maginot, Moore & Beck LLP

(57) ABSTRACT

A method for acquiring an X-ray image of anatomical features and surgical effectors in a surgical space of a patient includes detecting a particular pose of a particular C-arm used to acquire the X-ray of the surgical space. Characterization parameters of the particular C-arm in the particular pose are determined and incorporated into equations implemented in imaging software that is operable to generate an image of the anatomical features and surgical effectors in the surgical space. When the live X-ray of the surgical space is acquired, the imaging software generates a live image of the anatomical features and surgical effectors as a function of the characterization parameters to account for potential deviations due to the pose of the C-arm. In another feature, a potential error in the imaging process can be visually or automatically detected.

8 Claims, 8 Drawing Sheets

(51) Int. Cl.
*A61B 6/50* (2024.01)
*A61B 90/00* (2016.01)

(56) References Cited

U.S. PATENT DOCUMENTS

| | | | |
|---|---|---|---|
| 10,825,177 | B2 | 11/2020 | Isaacs et al. |
| 2011/0004431 | A1* | 1/2011 | Ringholz ............ A61B 6/4441 702/94 |
| 2013/0245477 | A1 | 9/2013 | Brodnick |
| 2019/0099142 | A1 | 4/2019 | Sato et al. |
| 2021/0298838 | A1 | 9/2021 | Isaacs et al. |

* cited by examiner

IMAGING SYSTEM AND METHOD FOR IMAGE LOCALIZATION OF SURGICAL EFFECTORS USING C-ARM CHARACTERIZATION PARAMETERS

BACKGROUND

A typical imaging system 100 is shown in FIG. 1. The imaging system includes a base unit 102 supporting a C-arm imaging device 103. An exemplary C-arm, shown detail in FIG. 2, includes a radiation source 104 that is positioned beneath the patient P and that directs a radiation beam upward to the receiver 105. It is known that the radiation beam emanated from the source 104 is conical so that the field of exposure may be varied by moving the source closer to or away from the patient. The source 104 may include a collimator that is configured to restrict the field of exposure. The C-arm 103 may be rotated about the patient P in the direction of the arrow 108 for different viewing angles of the surgical site. In some instances, metal or radio-dense material effecters, such as implants or instruments T, may be situated at the surgical site, necessitating a change in viewing angle for an unobstructed view of the site. Thus, the position of the receiver relative to the patient, and more particularly relative to the surgical site of interest, may change during a procedure as needed by the surgeon or C-arm technologist. Consequently, the receiver 105 may include a tracking target 106 (FIG. 1) mounted thereto that allows tracking of the position of the C-arm using a localizer system or tracking device 130. For instance, the tracking target 106 may include several infrared emitters spaced around the target, while the tracking device is configured to triangulate the position of the receiver 105 from the infrared signals emitted by the element. The base unit 102 includes a control panel 110 through which a radiology technician can control the location of the C-arm, as well as the radiation exposure. A typical control panel 110 thus permits the technician to "shoot a picture" of the surgical site at the surgeon's direction, control the radiation dose, and initiate a radiation pulse image.

The receiver 105 of the C-arm 103 transmits image data to an image processing device 122. The image processing device can include a digital memory associated therewith and a processor for executing digital and software instructions. The image processing device may also incorporate a frame grabber that uses frame grabber technology to create a digital image or pixel-based image for projection as displays 123, 124 on a display device or graphical interface 126. The displays are positioned for interactive viewing by the surgeon during the procedure. The two displays may be used to show images from two views, such as lateral and AP, or may show a baseline scan and a current scan of the surgical site. An input device 125, such as a keyboard or a touch screen, can allow the surgeon to select and manipulate the on-screen images. It is understood that the input device may incorporate an array of keys or touch screen icons corresponding to the various tasks and features implemented by the image processing device 122. The image processing device includes a processor that converts the image data obtained from the receiver 105 into a digital format. In some cases, the C-arm may be operating in the cinematic exposure mode and generating many images each second. In these cases, multiple images can be averaged together over a short time period into a single image to reduce motion artifacts and noise.

Standard X-ray guided surgery typically involves repeated x-rays of the same or similar anatomy as an effecter (e.g.—screw, cannula, guidewire, instrument, etc.) is advanced into the body. This process of moving the effecter and imaging is repeated until the desired location of the instrument is achieved. This iterative process alone can increase the lifetime risk of cancer to the patient over 1% after a single x-ray intensive intervention.

Classic image guided surgery ("IGS") uses prior imaging as a roadmap and projects a virtual representation of the effecter onto virtual representations of the anatomy. As the instrument is moved through the body, the representation of the effecter is displayed on a computer monitor to aid in this positioning. The goal is to eliminate the need for x-rays. Unfortunately, in practice, the reality of these devices doesn't live up to the desire. They typically take significant time to set-up, which not only limits adoption but only makes them impractical for longer surgeries. They become increasingly inaccurate over time as drift and patient motion cause a disassociation between physical space and virtual space. Typical IGS techniques often alter work flow in a significant manner and do not offer the physician the ability to confirm what is occurring in real-time and to adjust the instrument as needed, which is a primary reason fluoroscopy is used.

What would benefit greatly the medical community is a simple image localizer system that helps to position instruments without altering workflow. It would be substantially beneficial if the system can quickly be set-up and run, making it practical for all types of medical interventions both quick and protracted. The desirable system would significantly limit the number of x-rays taken, but does not require eliminating them. Therefore, by both encouraging reimaging and using this as a means to recalibrate, the system would ensure that the procedure progresses as planned and desired. Using the actual x-ray representation of the effecter rather than a virtual representation of it would further increase accuracy and minimize the need for human interaction with the computer. If the system mimics live fluoroscopy between images, it would help to position instruments and provide the accuracy of live imaging without the substantial radiation imparted by it.

SUMMARY

According to one aspect of the present disclosure, a method is provided for acquiring an X-ray image of anatomical features and surgical effectors in a surgical space of a patient in which the image is adjusted based on characterization parameters of the imaging device or C-arm. The method comprises detecting the position of one or more surgical effectors in the surgical space and generating position data therefor, and detecting a particular pose of a particular C-arm for acquiring a live X-ray of the surgical space. The particular C-arm includes an X-ray emitter and an X-ray detector, in which the detector includes an array of a plurality of pixels activatable by an X-ray cone beam emanating from the emitter.

In one step of the method, characterization parameters of the particular C-arm in the particular pose are determined, and those characterization parameters are incorporated into one or more equations implemented in imaging software that is used to generate an image of the anatomical features and surgical effectors in the surgical space detected by the particular C-arm. The image is represented by pixels of the detector activated by the X-ray beam, and the locations of the pixels are determined by the one or more equations as a function of the position data and the characterization parameters of the particular C-arm in the particular pose. The characterization parameters including a plurality of parameters that are unique to the particular C-arm and dependent on the pose of the C-arm. The one or more equations are operable to determine the locations of the pixels corresponding to the anatomical features and the surgical effectors detected by the X-ray cone beam in the surgical space.

After a live X-ray of the surgical space has been acquired, the imaging software is operated to generate a live image of the anatomical features and surgical effectors in the surgical space based on the locations of the pixels activated by the X-ray cone beam as determined by the one or more equations as a function of the characterization parameters. This live image is displayed for use by the surgeon during the surgical procedure.

In another aspect of the disclosure, a method for generating a display of an image of a patient's internal anatomy and of one or more radio-dense effecters in a surgical field during a medical procedure, comprises acquiring a baseline image of the surgical field including the patient's anatomy, using the C-arm, acquiring an image of the radio-dense effecter in the surgical field, independent of the baseline image, and then displaying an overlaid image including the image of the radio-dense effecter overlaid on the baseline image of the surgical field with the image of the radio-dense effecter positioned relative to the image of the patient's anatomy in the same manner as the actual radio-dense effecter is positioned relative to the actual anatomy. In a further step of the method, the position and movement of the radio-dense effecter is tracked, and in the overlaid image, the image of the radio-dense effecter is moved in accordance with the tracked movement of the radio-dense effecter.

In one aspect of the present disclosure, the method further comprises using tracking information from the tracking system to determine the position of the X-ray detector and the position of the radio-dense effector relative to the position of the X-ray detector. Tip indicia is displayed on the overlaid image, in which the tip indicia correspond to the position of the tip of the radio-dense effector relative to the position of the X-ray detector on the overlaid image. The tip indicia can be used to visually detect an error in the imaging system if the location of the tip indicia on the overlaid image does not align with the tip of the radio-dense effector in the overlaid image.

DETAILED DESCRIPTION

A computer-assisted imaging localization system is disclosed in U.S. Pat. No. 10,441,367 (the '367 patent), which issued on Oct. 15, 2019, that assists the physician in positioning implants and instruments within a patient's body. The disclosure of the '367 patent is incorporated herein by reference. The system has the desired effect of displaying the actual instrument or implant and using this displayed image to guide surgery without the need to directly interact with the computer. The system does so by displaying and moving overlapping images on a computer screen, allowing one image to be seen through the other. These image "masks" can be the unaltered image or doctored images to intensify or mitigate the anatomical or non-anatomical aspects of the image. Sliding these images over one another can help to position medical devices with a high degree of accuracy with a limited number of additional x-rays.

As described in the '367 patent, an initial X-ray image of the surgical site is obtained as a "localizing shot" or "baseline image". The image processing device 122 generates a digital image that can be displayed and manipulated digitally. With the anatomy identified and displayed on a computer screen, a "new" image with the effecter or instrument T is taken, with this image also converted to a digital image by the image processing device 122. This new image is displayed on top of the original localizing shot so that the resulting image looks like the conventional image on a fluoroscope screen. The effecter T incorporates fiducials or markers that are trackable by the localizer system 130 capable of tracking movement of the effecter. The 3D movement of the effecter measured by the localizer system can be applied to the digital representation of the "new" image relative to move the "new" image relative to the "localizing shot" image, as illustrated in the images of FIGS. 3A-3D. Thus, as the tip of the effecter is tracked, the movement of the "new" image shows the change in position of the tip of the instrument being tracked relative to the stationary anatomy depicted in the "localizing shot". On the computer screen, it thus appears as if live fluoroscopy is being taken as the effecter is being moved and as if the actual tool or implant is being moved and adjusted relative to the patient's anatomy. When the next image is taken, the tip of the effecter is at the location that the physician desires.

Figures 3A, 3B, 3C, 3D:
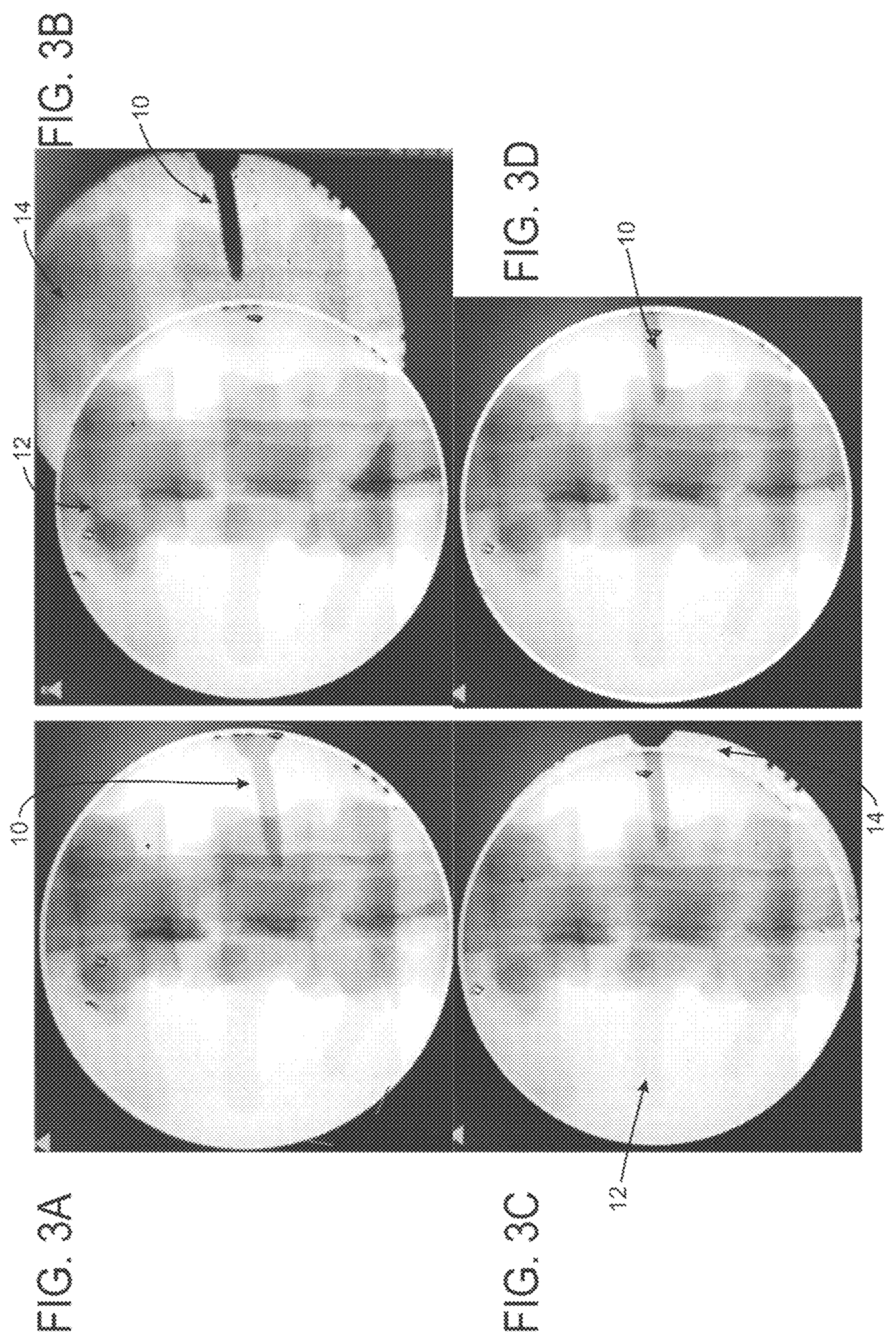
FIGS. 3A-3D are screen shots of image displays of a surgical site showing the patient's anatomy and a movable image of a radio-dense effecter in relation to a fixed image of the surgical site.

In the example shown in FIGS. 3A-D, a bone screw 10 to be tracked is introduced into a patient after an initial "localizing shot" and projected on the display 122/123 (FIG. 1) as the screen shot of FIG. 3A. As the tracked instrument 10 is moved out of the field of the localizing shot or baseline image 12, as depicted in the screen shot of FIG. 3B, the two overlapping images can be appreciated, with the localizing shot 12 seen to the left and the new low radiation image 14 to the right. When the tracked screw is moved into an ideal location based on the desire of the physician, such as shown in the screen shot of FIG. 3C, the image on the screen can constantly project an overlaid image (overlaying the full dose localizing shot 12 with the low dose image 14) that replicates what a new fluoroscopic image would look like at any point, mimicking live fluoroscopy without obtaining a new live image. It can be appreciated that the localizing or baseline image 12 does not change as the effecter 10 is moved, at least so long as the C-arm or X-ray source is not moved. Thus, the digital data for the localizing image 12 is not manipulated by the image processing device during movement of the effecter. On the other hand, the image processing device does manipulate the digital data of the "new" image based on the projected movement of the tracked effecter so that the "new" image moves across the display as the effecter is moved. It can be appreciated that the "new" image can be used as a new baseline image upon which an even new image can be overlaid in the same manner. It can also be appreciated that the "new" image need not be a low dose image.

A stationary full dose new image can be taken, such as the display in the screen shot of FIG. 3D, to confirm that the effecter 10 is in the location desired by the physician. If for some reason the image alignment is off or further fine tuning is required, this newly acquired image can replace the prior localizing shot image as the baseline image, and the process is repeated. The system thus resets or recalibrates when the full dose new image is taken, so that subsequent images are always more accurately displayed than previous ones. It is contemplated that the recalibration image may be less than a full dose image, since the recalibration process can be independent of the dosage of the images.

As the physician moves the effecter 10, the "new" image moves with the effecter, which image can be a low dose image as desired. When the effecter is within the field of the baseline or localizing shot image, as in FIG. 3C, the image of the effecter from the low dose image is combined with the stationary localizing image so that the physician can clearly see the patient's anatomy and the effecter's position relative to that anatomy. As the effecter is moved within the field of the baseline image, the image of the effecter (and the "new" image) moves accordingly so that the physician can guide the tip of the effecter to the desired position in the anatomy. The movement of the "new" image on the display is based on the geometry of the tip of the effecter relative to the location within the cone beam of the fluoroscope. The position of the effecter/instrument T can be recalibrated on each new X-ray shot. On the instrument side this means that each x-ray resets the relative position or the initial starting point of the "new" image to the current location of the tracked effecter to which is linked a "new" image with that effecter in it.

Figure 4:
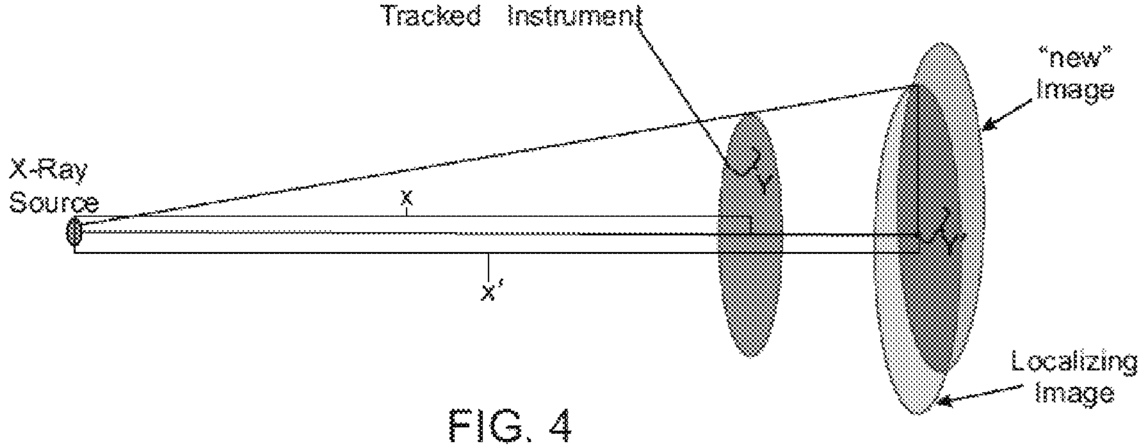
FIG. 4 is a diagram of steps in displaying movement of a tracked effecter on an x-ray image of a surgical site.

The movement of the "new" image on the display is based on the geometry of the tip of the effecter relative to the location within the cone beam of the fluoroscope, as depicted in FIG. 4. The nearer the tip of the tracked effecter is to the x-ray source, for the same relative movement, the greater the movement of the "new" image and therefore the effecter's projection (in pixels) relative to the size of the "localizing shot". Assuming a standard size image, such as a 9 in. image intensifier, and assuming a typical 1000 mm separation of the x-ray source from the intensifier, there is an approximate 2.24 pixel per mm movement of the tracked effecter projected on the image intensifier. Away from the image intensifier and closer to the source, this pixel-per-mm movement ratio is magnified in a consistent manner as shown in FIG. 4. In particular, the movement distance of the projection of the tracked effecter on the image intensifier is given by $Y'=X'*Y/X$, where Y is the actual movement distance of the effecter, X is the distance from the source to the tracked effecter/instrument, X' is the distance from the source to the localizing image at the image intensifier and Y' is the projected movement distance. It can be appreciated that the distance X' is typically fixed throughout the procedure for a conventional C-arm X-ray source. The distance X and the movement distance Y can be determined by the image processing device 122 (FIG. 1) based on data received from the localizer system used to track the movement of the effecter. The image processing device uses the projected movement distance Y' to move the "new" image accordingly on the display.

It can be appreciated that it is very important that the X-ray image of the surgical site and the effector be as accurate as possible. It is further important that the X-ray image be registered to an established frame of reference that is fixed relative to the patient, so that movements of the surgical effector are accurately depicted on the display being used by the surgeon to guide the effector. As is known, the receiver or detector 105 of the C-arm includes an array of pixels that are activated by the X-ray beam generated by the source 104. The pixels thus have a fixed position relative to an established frame of reference, namely the C-arm, so the physical location of an object detected by the X-rays can be established in the displayed image based on the position of the activated pixel. However, every X-ray device has inherent characteristics that cause the acquired image to deviate from the actual anatomy and effector geometry, such as image distortion and warping of the acquired image. It is thus important that the imaging device or C-arm be calibrated so that pixels in the X-ray image (or voxels, depending on the nature of the image) can be corrected as needed to make the acquired image as accurate as possible.

The imaging system of the present disclosure contemplates a system for clearly informing the surgeon when the imaging and navigation systems are not in sync. The accuracy of an image guidance system during any surgical procedure can degrade over time. Errors of this nature can include disassociation of the actual anatomy from the imaging data set caused when the anatomy moves relative to the fixed reference for the C-arm and navigation system—i.e., the position of the patient has shifted on the OR table. Other errors can occur when the reference frame has shifted, such as by bumping into the C-arm. Errors in calibration of the imaging or navigation systems are also sources of discrepancies between the actual surgical site and the representation of the surgical site presented to the surgeon to help guide the surgical procedure. In prior image guidance systems, the only check on continuing accuracy of the system has been to place an instrument onto a known anatomical feature or reference structure to see if the system accurately depicts the location of the instrument on the X-ray. But in these prior systems, there is nothing to prompt an accuracy check, other than the surgeon's intuition, a pre-planned accuracy check protocol or the visual appearance of a clear error.

One feature of the present imaging system is that it provides a means for the surgeon to identify when the system accuracy is starting to go awry. According to the present system, the location and trajectory of an instrument or effector in the surgical field is superimposed on the X-ray image of the surgical site. As described above, the instrument or effecter T incorporates fiducials or markers that are trackable by the localizer system 130 capable of tracking movement of the effecter. Thus, the 3D position and orientation of the effector T is known. Likewise, 3D position of the X-ray image can be acquired by the localizer system or other tracking device. For example, as described in more detail below, a calibration collar 150 can be mounted on the detector housing of the C-arm, with fiducials on the housing that can be detected by the localizer system 130. With that information, the imaging system of the present disclosure "knows" where the effector T is located and how it is oriented in the Xray image.

Figure 5:
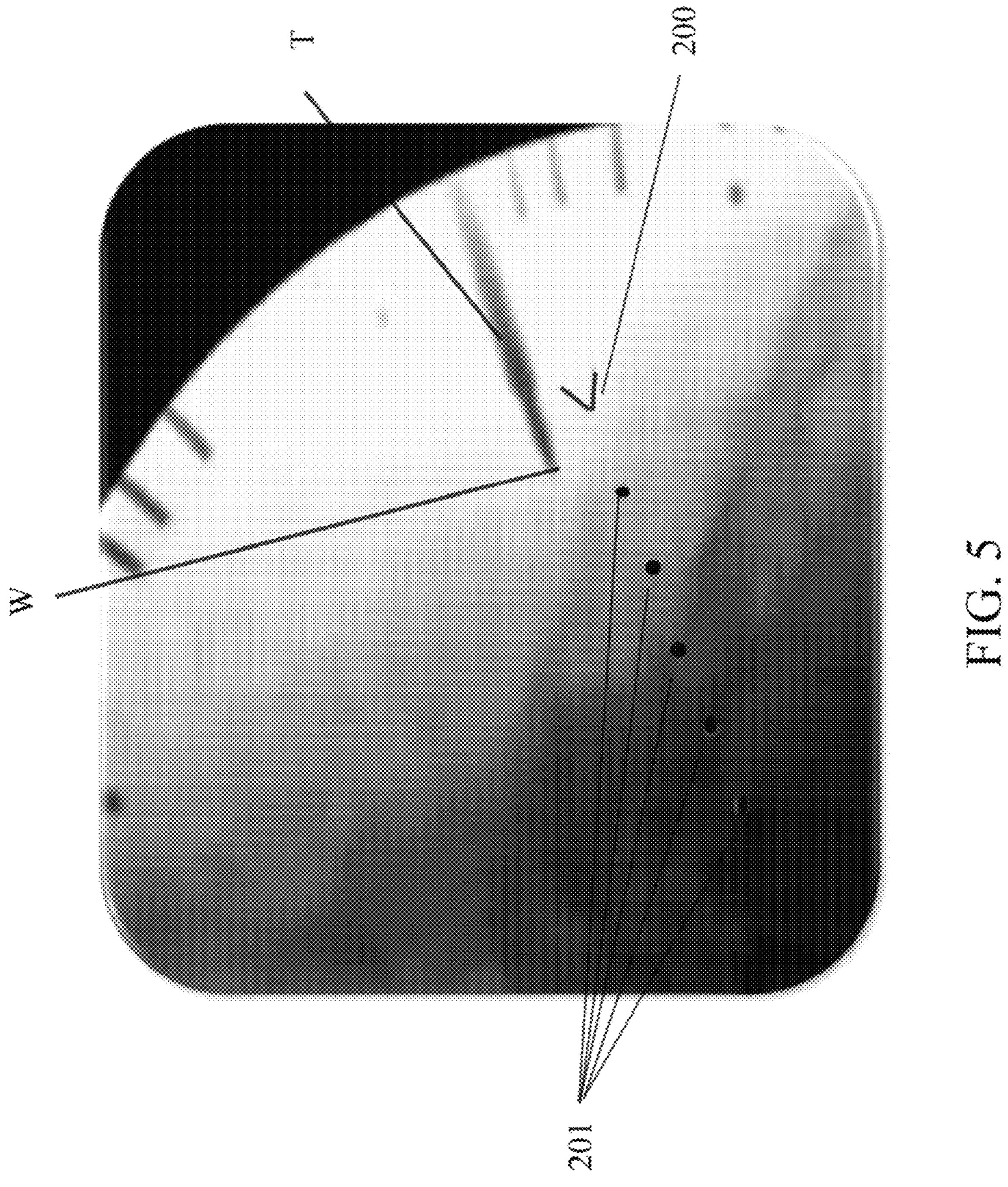
FIG. 5 is an X-ray image of surgical site including a tool with a chevron feature according to the present disclosure.

The imaging system generates an indicia 200, as shown in FIG. 5, indicative of the location of the working tip of the instrument or effector, based on the tracking information. The trajectory of the effector is represented by another indicia, such as the series of dots 201 that extend from the tip indicia, as shown in FIG. 5. These indicia 200, 201 are displayed on the X-ray image presented to the surgeon. As described above, this X-ray image includes an image or representation of the instrument or effector T and the working tip W of the effector overlaid on an image of the anatomy, with the image of the effector moving as the physical effector is moved by the surgeon. As shown in FIG. 5, the working tip W and indicia 200 are not aligned, and the trajectory indicia 201 are not aligned with the trajectory of the image of the effector T. In this case, the surgeon is immediately aware that the tracking and imaging features are not in sync, or are not properly calibrated.

Figure 6:
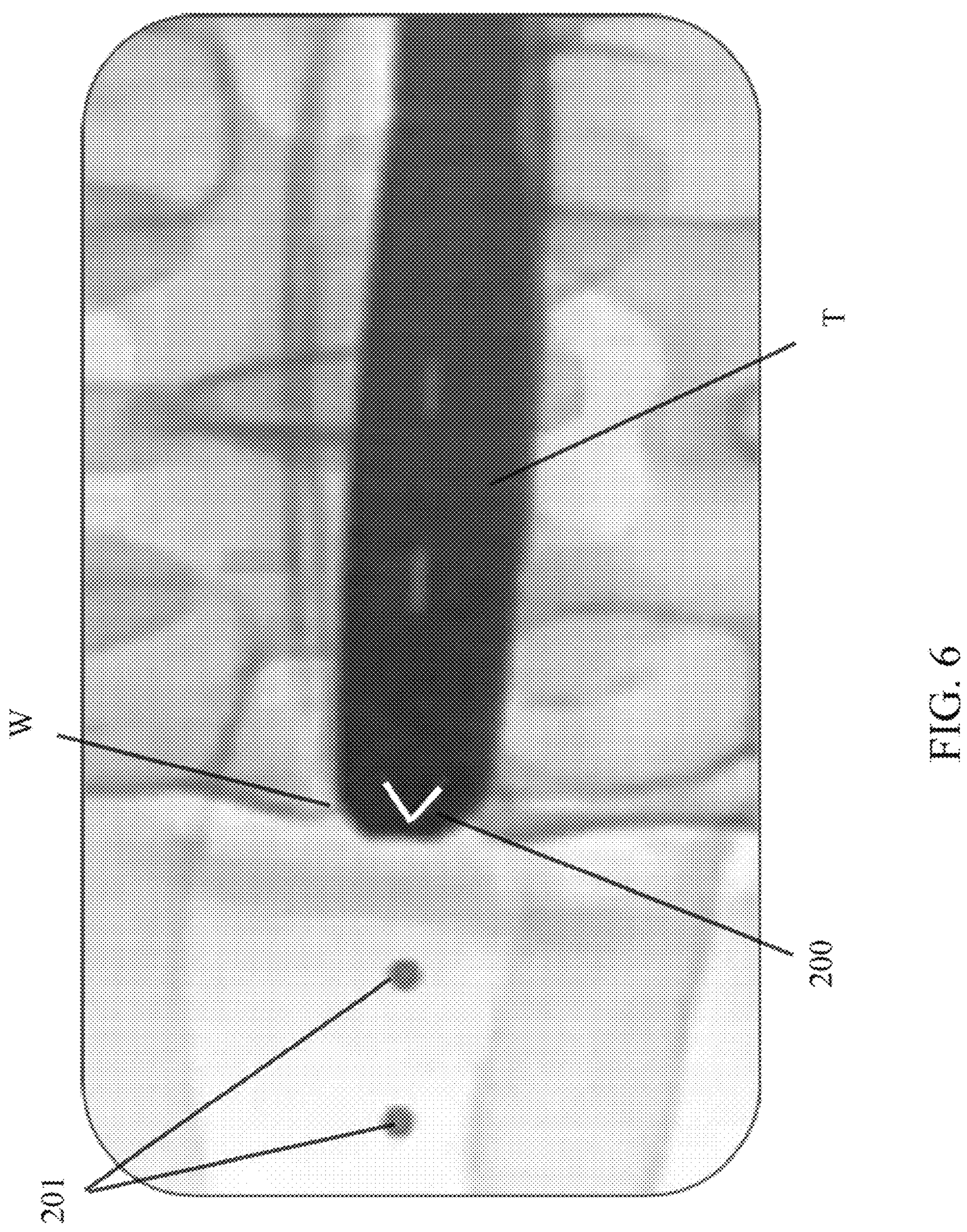
FIG. 6 is an enlarged X-ray image of the working end of a tool with the chevron feature.

On the other hand, proper calibration can be demonstrated when the tip indicia 200 is oriented at the working tip W of the image of the effector and the trajectory indicia 201 are aligned with the longitudinal axis of the effector T, as shown in FIG. 6. In the illustrated embodiment, the tip indicia 200 is in the form of a chevron to enhance the visibility of the indicia overlaid on the X-ray image. The trajectory indicia 201 can be solid dots that are readily visible but don't interfere with the view of the underlying anatomy.

During a procedure, the surgeon will move an effector relative to the surgical site. As described in the '367 patent, a localizer or tracking system tracks the movement of the effector and the imaging software translates that movement in the tracking system coordinate system to a comparable movement in the coordinate system of the C-arm, and ultimately into a movement in the acquired X-ray image. As discussed above, this movement is captured visually by overlaying the image of the surgical site with the effector over a baseline image. As the effector is moved, the localizer tracks its movement and the imaging system moves the overlaid indicia 200, 201 accordingly. In a properly calibrated system, the movement of the indicia and effector T on the overlaid image will coincide, so the tip indicia 200 will shadow the movement of the working tip W of the effector T. Any disassociation between the indicia and the X-ray image of the effector signals a problem. The indicia 200, 201 therefore provides a clear visual cue to the surgeon or C-arm operator that there is a discrepancy in the imaging system and/or racking system.

If the indicia and working tip do not coincide, the first response can be to take a new X-ray of the surgical site. If the apparent lack of calibration is due to movement of the patient or the frame of reference, a new X-ray will realign the image to the actual patient anatomy. In this case, there is no calibration error between tracking and imaging, so it is only necessary to re-register the X-ray image to the actual anatomy. If the indicia and working tip are still not aligned, then the system can stop tracking the effector and issue a warning to the surgeon.

As described above, the indicia 200, 201 provide a visual indication to the surgeon whether the imaging and/or tracking systems are properly calibrated. The goal is to ensure that the position and orientation of the surgical effector in the overlaid X-ray image relative to the anatomy is correct, at least within an acceptable margin, such as 2-3 mm.

In another approach, the working tip of the image of the effector in an X-ray image can be detected and located in the C-arm coordinate system. One approach for locating the working tip of the effector in an X-ray image is described in the '367 patent, the disclosure of which is incorporated herein. This approach relies on analysis of the pixels of the X-ray image to identify radio-dense features, such as a surgical effector. The imaging software can isolate the tip of the radio-dense feature and locate the tip in the C-arm coordinate system based on the location of the pixels of the detector array corresponding to the tip in the detector array. The location of each pixel in the detector array in the C-arm coordinate system is known, so the position of the tip in the C-arm coordinate system is known. The physical tip of the actual effector can be detected by the localizer or tracking system, as described above, and its position in the C-arm coordinate system can be derived from the tracking system data. Two coordinates are generated—one corresponding to the location of the tip in the X-ray image and the other corresponding to the expected location of the tip from the physical position of the actual effector. Those coordinates are compared and it they deviate by a predetermined amount, the imaging software can generate a warning condition, which can include issuing a warning and/or initiating diagnostic and/or corrective actions to isolate and correct the source of error, if possible. As suggested above, the deviation range can be 2-3 mm before an error is identified.

It can be appreciated that the indicia 200, 201 and method just described can be used to determine whether the position of the effector tip derived from registered navigation information is in sync with the actual position of the tip in a new X-ray. The navigation information can provide the location of the tip as determined by the localizer. The tip detection software described above can determine the location of the effector tip in the new X-ray and can enhance the appearance of the tip in the imaging information for the new X-ray. The indicia 200, 201, as determined by the navigation or tracking software, can be overlaid on the new X-ray image to give the surgeon an immediate indication of whether the navigation information is in sync with the imaging information. Alternatively, the pixel location of the tip generated from the navigation information can be compared to the pixel location of the tip generated by the tip detection software applied to the new X-ray. If the deviations between the pixel locations fall within the desired range, the system can provide a notification to the surgeon. Alternatively, if the deviation exceeds the desired range, a warning can be issued and/or diagnostics initiated and/or corrective actions taken.

Figure 7:
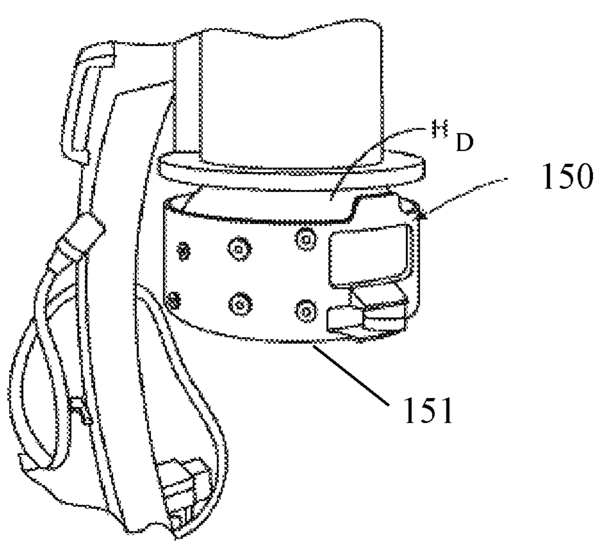
FIG. 7 is a perspective view of the X-ray detector shown in FIG. 2, with a calibration collar mounted thereon.
Figure 8:
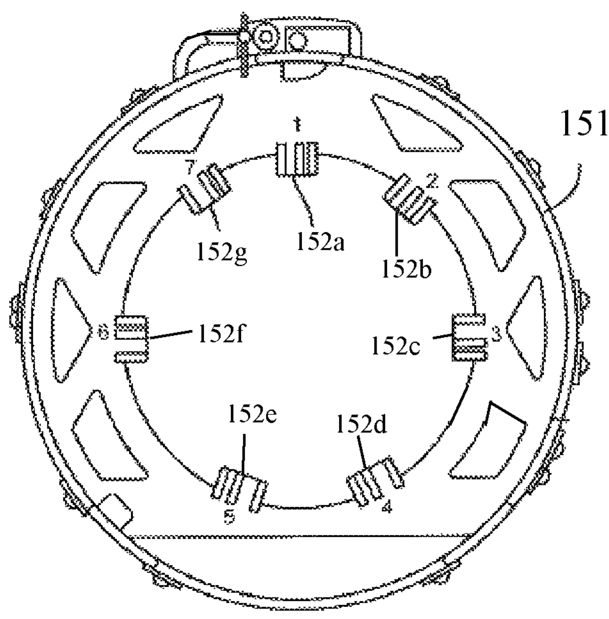
FIG. 8 is a bottom view of the calibration collar shown in FIG. 7.

Calibration of the C-arm can be achieved using a calibration collar 150 that is configured to be mounted on the detector housing HD of the C-arm (FIG. 7) with the end face 151 of the collar flat with the end face of the housing. The end face 151 includes a plurality of unique glyphs 152*a*-152*g* that are detectable by the receiver 105, as shown in FIG. 8. The glyphs are positioned around the perimeter of the collar so that they do not interfere with the image of the surgical site. The glyphs can be metallic rods that are detectable by the X-ray. The 3D position of each of the glyphs relative to the C-arm is fixed and known.

Figure 9:
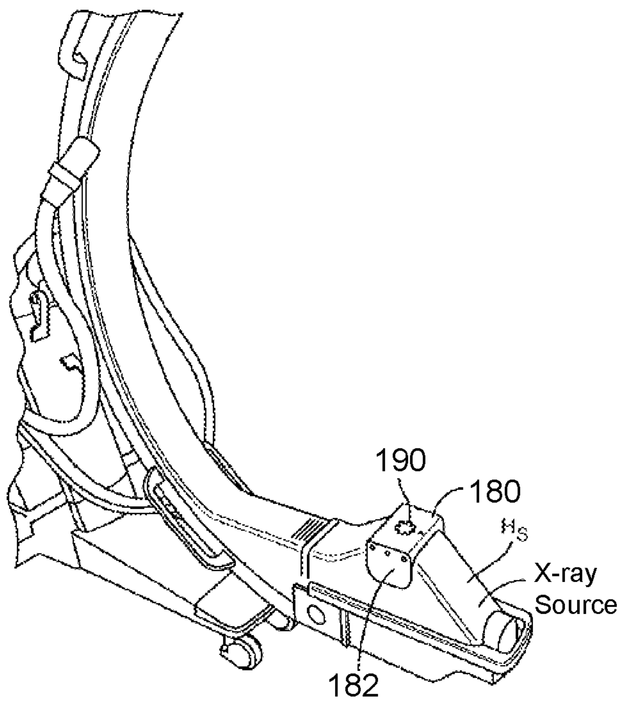
FIG. 9 is a perspective view of the X-ray source for the C-arm device shown in FIG. 2, shown with a source calibration device mounted thereon.
Figure 10:
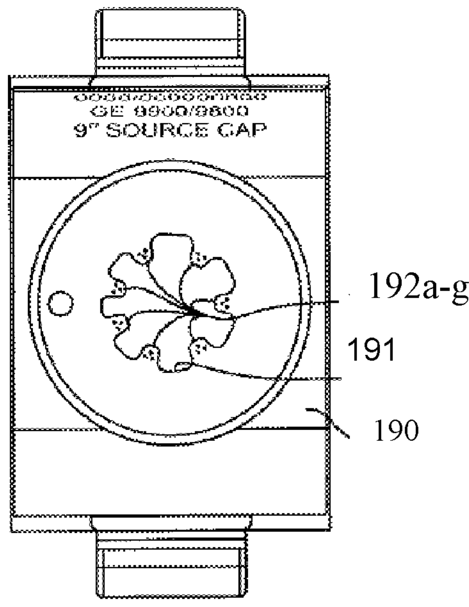
FIG. 10 is a top view of the source calibration device shown in FIG. 9.

The C-arm calibration process also involves calibration of the X-ray source, either separate from or together with calibration of the detector. To that end, a source cap 180 is provided that is configured to be mounted over the housing $H_D$ of the C-arm, as shown in FIG. 9. The cap includes a U-shaped body 182 that is sized to be seated on the output face of the source housing $H_S$. The U-shaped body 182 includes a calibration plate 190 (FIG. 10) that is seated flush with the output face of the source housing $H_S$. The plate defines an opening 191 that is aligned with the beam transmission path to the X-ray detector of the C-arm device. The plate further defines a plurality of glyphs 192*a*-*g* that extend radially into the opening 191 so that the glyphs intersect the beam transmitted by the X-ray source. As with the glyphs 152, the glyphs 192 are detectable by X-ray. In addition, the 3D position of each of the glyphs of the source cap relative to the C-arm is fixed and known. Thus, if the movement and position of the C-arm is known, the expected orientations and positions of the two sets of glyphs 152, 192 are known. Details of the calibration collar, source cap and glyphs are disclosed in U.S. Pat. No. 10,825,177 (the '177 patent), which issued on Nov. 3, 2020, the disclosure of which is incorporated herein by reference.

In one aspect of this disclosure, the glyphs can be made of low radio-dense material such that they only appear in an X-ray image when imaging extremely low-density material (air and plastic) and become invisible to the X-ray imaging when imaging higher radio dense material (such as human anatomy and surgical effectors). This feature allows the collar and cap to be fixed to the C-arm at all times rather than removed prior to a live procedure. As an alternative, the glyphs can be replaced with holes/gaps in the collar/cap material. These holes/gaps would show up as lighter objects that can still be identified just like the radio-opaque glyphs for characterization purposes.

The C-arm, and/or calibration collar and source cap, are provided with fiducials or markers, such as the tracking target 106 (FIG. 1) that are detectable by the localizer system or tracking device 130. (It is contemplated that other forms of detection can be implemented that allow the components of the system, as well as surgical instruments and implants, to be accurately tracked at the surgical site.) Thus, the spatial position and orientation of the C-arm can be known when an X-ray image is acquired. The image processing device 122 is configured to identify the glyphs 152 of the calibration collar 150 and the glyphs 192 of the source cap 180 in the X-ray image for calibrating the C-arm. In particular, the processing device executes software that finds the pixel locations in the X-ray detector pixel array of the receiver 105 that correspond to the metallic rods and/or beads forming the glyphs.

Figure 1:
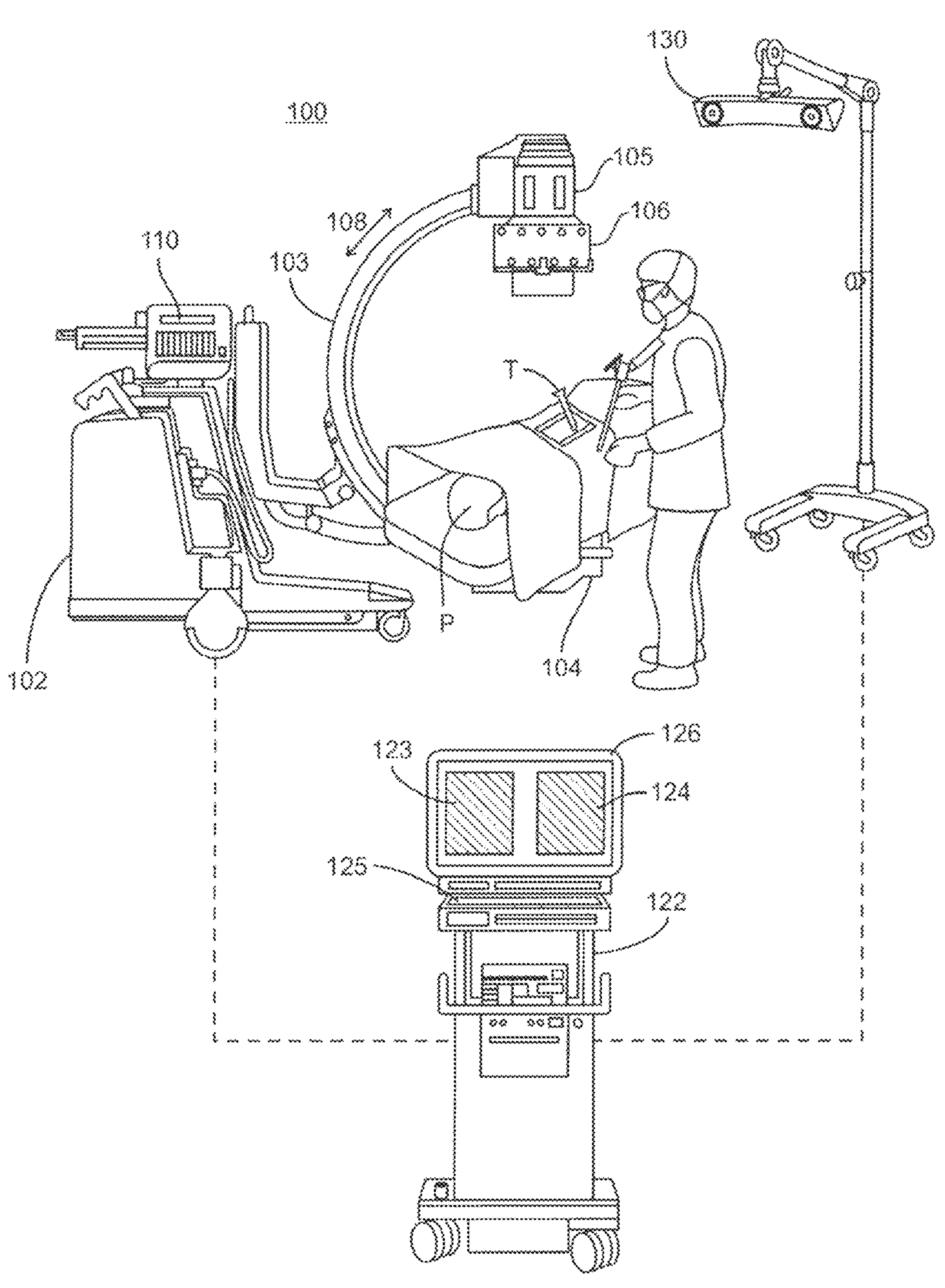
FIG. 1 is a pictorial view of an image guided surgical setting including an imaging system, an image processing device and a localizer or tracking device for surgical instruments and devices.
Figure 2:
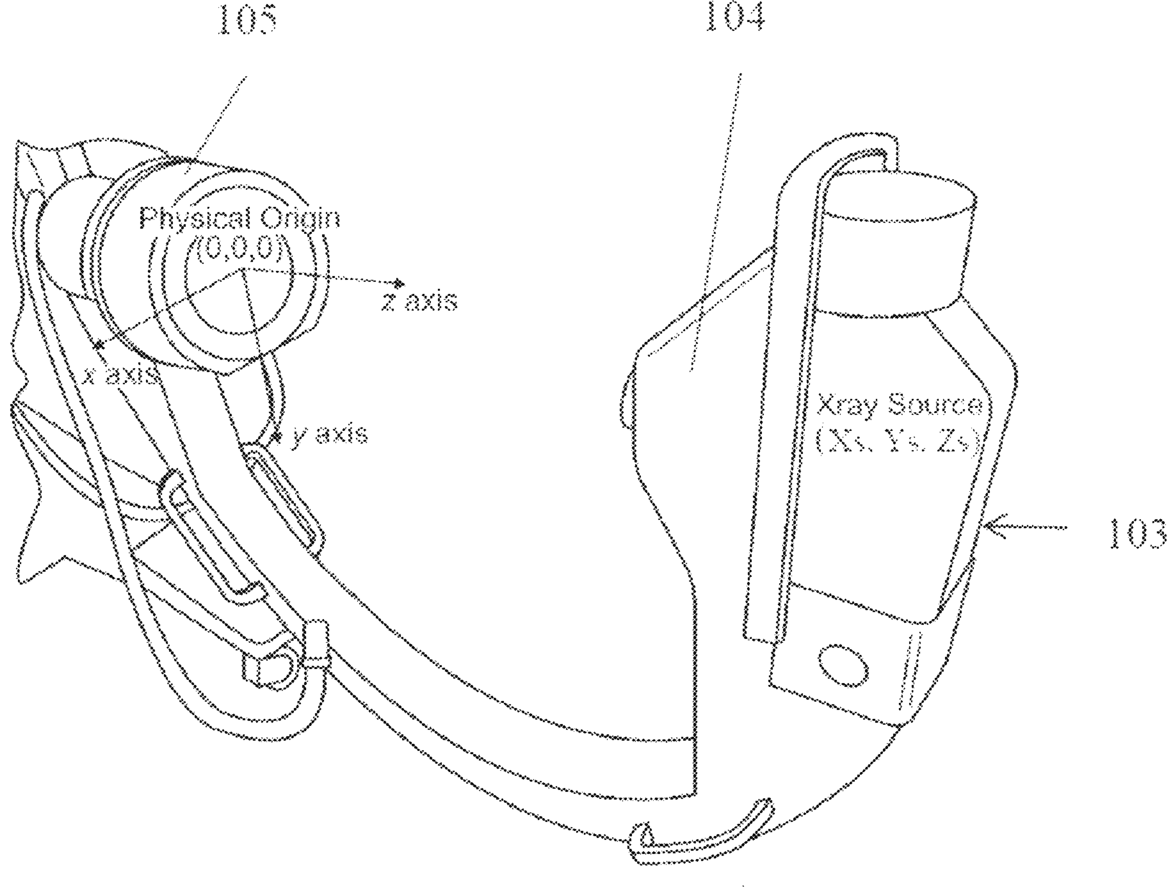
FIG. 2 is a perspective view of a conventional C-arm x-ray device showing the system coordinates superimposed thereon.

As represented in FIG. 4, the X-ray beam is an expanding cone from the source to the receiver or image intensifier. The calibrated C-arm assumes a fixed position of the beam cone throughout a surgical procedure. However, as the C-arm moves, deviations in the cone beam can occur—the beam may shift in the X and Y directions relative to the receiver. Thus, the cone beam orientation can be pose specific. A "pose" of the C-arm is the global position or orientation of the C-arm relative to a globally fixed position, such as the floor of the OR. It can be appreciated that the pose of the C-arm is determined independent of the pose or position of the patient, whether prone, supine or lateral. In order to ensure accurate depiction of the surgical site and the movement of the tracked effectors, the effect of the C-arm pose on the cone beam must be established. Thus, the method of the present disclosure "characterizes" the C-arm in one or more poses of the C-arm. As used herein, "characterization" is a process to determine the properties or characteristics of a C-arm that affect X-ray cone beam and ultimately the accuracy of an image acquired by the C-arm. One pose of the C-arm 103 is shown in FIG. 1 in which the emitter and detector are essentially directly vertically aligned over the patient to acquire an AP image. However, during a typical surgical procedure, different images of the surgical site are required to help the surgeon accurately visualize the site, ranging from lateral to AP images. Thus, the C-arm may be rotated relative to the patient in the direction of the arrow 108, in particular about a global x-axis. It is understood that some C-arms permit rotation in additional degrees of freedom, such as about the global y- and z-axes. The global position of the C-arm, or pose, can be determined from position detectors on-board the C-arm, by a tracking system that tracks fiducials on the C-arm, and/or by a gyroscopic system.

In an ideal condition, the physical geometry of the C-arm, and thus of the X-ray cone beam generated and detected by the C-arm, does not change regardless of the physical orientation or pose of the C-arm. Of course, in reality, gravity and the physical properties of the C-arm structure mean that the physical geometry of the C-arm will change based on pose or orientation of the C-arm. For instance, it is known that a typical C-arm will bow outward (expanding the C-shape) when the C-arm is positioned for a lateral image, and will condense (reducing the C-shape) when the C-arm is positioned for an AP image. This bowing and condensing of the C-arm results in subtle changes in geometry of the X-ray beam so that the location of the receiver 105, and detector array, relative to the source 104 changes. Moreover, C-arms are susceptible to image distortion (such as pinwheel and pincushion), warping, detector pixel offset, detector rotation, pixel aspect ratio, source location errors, deformation or sagging over time, damage and the like These error sources are different among C-arms. Thus, it is important to characterize each C-arm to ensure optimum imaging during surgical procedures.

In an exemplary system, each pixel is identified by coordinate pair (u,v), which is related to physical space by the pixel coordinate ($u_0$,$v_0$) of the physical origin (0,0,0) at the center of the collar, the physical increment p between pixels (expressed as pixels/mm), and the aspect ratio r between the vertical pixel increment and the horizontal pixel increment. Additionally, the C-arm allows the user to rotate the X-ray image arbitrarily by some angle a. Moreover, there may be distortion on the X-ray detector so that the pixels do not conform to the rectilinear grid, which can be modeled as an angular component $\alpha_d$ and a radial component $r_d$. These values—p, r, ($u_0$,$v_0$), a, $\alpha_d$, $r_d$—as well as the (X, Y, Z) location of the emitter, the rotation angle of the detector and image distortion, constitute parameters that are determined in the characterization process. All of these parameters determine where the X-ray cone beam is oriented in the frame of reference of calibration collar or cap (which are, in turn, fixed to the C-arm). These parameters are used in equations that map a tracked surgical tool at a global location (x, y, z) to the pixel coordinate (u,v) of several pixels that form the image of the tracked tool. In one system, as disclosed in the '177 patent incorporated by reference, the equations can have the form of Equations (1) and (2) below:

$$p\begin{bmatrix} r & 0 \\ 0 & 1 \end{bmatrix}\begin{bmatrix} \cos a & \sin a \\ -\sin a & \cos a \end{bmatrix}\begin{bmatrix} z_s\left(\frac{x-x_s}{z_s-z}\right)+x_s \\ z_s\left(\frac{y-y_s}{z_s-z}\right)+y_s \end{bmatrix}+\begin{bmatrix} u_0 \\ v_0 \end{bmatrix}=\begin{bmatrix} u \\ v \end{bmatrix} \tag{1}$$

$$pe^{dr_d}\begin{bmatrix} r & 0 \\ 0 & 1 \end{bmatrix}\begin{bmatrix} \cos a & \sin a \\ -\sin a & \cos a \end{bmatrix}\begin{bmatrix} \cos da_d & \sin da_d \\ -\sin da_d & \cos da_d \end{bmatrix}\begin{bmatrix} x_d \\ y_d \end{bmatrix}+\begin{bmatrix} u_0 \\ v_0 \end{bmatrix}=\begin{bmatrix} u \\ v \end{bmatrix}, \tag{2}$$

where $$\begin{bmatrix} z_s\left(\frac{x-x_s}{z_s-z}\right)+x_s \\ z_s\left(\frac{y-y_s}{z_s-z}\right)+y_s \end{bmatrix}=\begin{bmatrix} x_d \\ y_d \end{bmatrix}$$

and $$\sqrt{x_d^2+y_d^2}=d.$$

Other equations can be utilized that incorporate these and other parameters that affect the coordinate pair for image pixels, such as for image distortion and warping. Ideally, the values for these parameters are fixed, or in some cases null, for all C-arms so that the pixel position calculated for any point on an imaged feature never varies. However, in reality, the characteristics of a C-arm can vary between C-arms and between poses of that C-arm. It can be appreciated that deviation of the presumed value for any of these parameters, such as $(u_0, v_0)$, p, r, $\alpha_d$ and $r_d$, from the actual values of these parameters can lead to associating the wrong pixel, identified by the coordinate pair (u, v), with a point on the object being tracked and imaged, leading to an offset of the image displayed for the surgeon and radiologist.

In accordance with the present disclosure, C-arm characterization is achieved with the fiducials or glyphs fixed to the C-arm emitter and detector—namely the calibration collar 150 (FIG. 7) and cap 180 (FIG. 9). In one approach, the C-arm is placed in a baseline pose, typically the pose shown in FIG. 1, and an image shot is taken. It should be appreciated that this X-ray image can be acquired independent of any live surgical procedure and prior to use of the C-arm in an actual procedure. Ideally, this C-arm characterization process is undertaken when a C-arm is delivered to the medical facility. The resulting characterization information can then be used whenever the C-arm is being used. However, it is contemplated that in some cases the characterization X-ray can be an image acquired during a surgical procedure.

When the X-ray image is taken, a frame of reference or coordinate system is associated with the fixed position of either the collar or the cap, such as the x-, y-, z-axes and the physical origin (0,0,0) at the center of the detector in FIG. 9. The locations of the beam source (Xs, Ys, Zs) and of the imaging pixel data of the detector are measured in this coordinate system. The pixels are oriented in an image plane, namely the x-y plane, and are optimally aligned in a rectilinear grid. The glyphs 152, 192 are identified in the X-ray image. Since the physical positions of the glyphs are known, the expected coordinates of the pixels representing those glyphs are also known. The values for these expected coordinates are used to determine the characterization parameters for the particular C-arm in the particular pose. In particular, the software of the image processing device is configured to calculate the characterization parameters, such as the parameters in Equations (1) and (2) above. These parameters are associated with the specific C-arm and the specific pose and stored in a database, which can be within the image processing device 122, within the C-arm control processor itself, or within a remote storage, such as a cloud data storage. The database thus contains a unique identifier for the specific C-arm, data for the pose of the C-arm, and characterization parameters obtained at the particular pose. The data can be global positioning data generated by a 3D tracking device, such as the device 130.

As discussed above, the calibration collar and cap are components that are mounted to the emitter and detector, respectively, of the C-arm. Each time these components are mounted to the C-arm, they may be mounted slightly differently, shifting or rotating from a previous mounted position. This offset in the mounting of the collar and cap does not alter the characterization parameters when they are determined in the characterization process; however, this offset will shift the frame of reference of the cap or collar relative to the X-ray images produced by the C-arm. Consequently, the characterization parameters can include the offset between the collar and the cap from the proper baseline position of the components. This offset can be applied to the equations used to generate the X-ray image, as discussed above. This offset can be measured physically and input into the imaging software, or can be acquired through an X-ray.

In some cases, the image distortion parameters applied in Equation (2), namely the angular component $\alpha_d$ and the radial component $r_d$, can be obtained using a BB plate integrated into or mounted on the collar 150 or cap 180 or a calibration phantom with a pattern of embedded BBs, using the techniques disclosed in the '177 patent. In those cases, a second X-ray at the particular pose can be obtained to visualize the BB array to determine the image distortion parameters. The image distortion parameters are stored in the database with the other characterization parameters. It is noted that not all C-arms will experience material image distortion, in which case the distortion parameters are not required.

The C-arm can be then moved to a different pose, such as rotation from an AP image position to a lateral image position. A new X-ray image of the glyphs (and, if necessary, the BB array) is taken and the characterization parameters are derived in the manner described above. Since these X-ray images are being acquired independent of a surgical procedure, multiple images can be obtained at multiple poses, with the object being to populate the characterization database with sufficient information to be able to extrapolate characterization parameters for a new C-arm pose during a surgical procedure. However, it can be appreciated that a C-arm can be moved to many positions during a procedure, most of which will not be identical to any of the poses used to generate the C-arm characterization parameters. In some cases, it may be necessary to interpolate the characterization parameters for a live X-ray pose from the stored characterization parameters. Preferably, if the current position of the C-arm is within a predetermined angle, such as within 3 degrees, of prior known position, interpolation is not necessary. In one embodiment, the global position of the C-arm pose in a live X-ray can be used to determine two or more previous characterization X-ray positions that are globally closest to the live X-ray pose. A linear interpolation can be used to estimate the characterization parameters from the stored characterization parameters.

In some cases, a live X-ray during the surgical procedure can be used to generate characterization parameters for the C-arm in a new pose during that procedure. Since the collar 150 and cap 180 are configured to avoid interfering with a live X-ray image of a surgical site, the collar and cap can be retained on the C-arm during the procedure. During the procedure, the characterization parameters are interpolated for the live image generation. During the procedure, the glyph-related information is stored for each pose of the C-arm when a live X-ray is taken. For any given live X-ray, the characterization parameters can be determined and applied to the above equations in tracking the movement of the surgical effector or instrument. Alternatively, or in addition, after the surgical procedure is finished, the accumulated pose data can be processed to determine the characterization parameters for each C-arm pose. Parameters are stored with previous characterization parameters in a database for use in improving the current procedure as well as for use in a subsequent live procedure. It can be appreciated that over time the database of characterization parameters will become heavily populated so that, at a minimum, the interpolation of new characterization parameters for a new pose will become more accurate, and at a maximum, any live C-arm pose will correspond to a stored pose.

It can be appreciated that the database within the image processing device can contain characterization parameters for multiple C-arms, with each C-arm assigned a unique identifier, such as a product serial number. Alternatively, a global database can be maintained separate from any image processing device, such as in cloud storage. The image processing device can be configured to automatically recognize a particular C-arm, such as by reading its unique identifier, and then can access the global database to obtain the characterization parameters for the particular C-arm. As a further alternative, the C-arm itself can maintain the database of unique poses and characterization parameters, and the image processing device can then read the characterization parameters when it is connected to the C-arm.

Ideally, every C-arm is characterized in the manner described above, and the characterization parameters for every C-arm is updated as new poses and characteristics parameters at the new poses are obtained. Each time the C-arm is used in a live procedure, the particular C-arm is identified by the unique identifier and stored characterization parameters can be accessed for that C-arm. In order to verify the accuracy of the stored characterization parameters, an X-ray shot can be taken prior to commencement of the live procedure, with the C-arm at one of the stored poses. If the characterization check is positive, meaning that the characterization parameters of the live shot match the stored parameters, the C-arm is ready for the live procedure.

In order to obtain the characterization check X-ray, the calibration collar 150 is mounted to the detector and the cap 180 is mounted to the X-ray source, as described above. In some cases, the collar and cap can be mounted slightly differently between procedures. If the collar is offset relative to the cap by a certain amount, such as by 2 mm, the offset does not change the stored characterization parameters but it does shift the frame of reference of the tracking object (collar or cap) relative to the X-ray images produced by the C-arm. In this instance, the characterization check will be negative, meaning that the characterization parameters will not match. The collar-to-cap offset can be either measured without an X-ray by physically measuring the offset or by comparing tracking data for the collar and cap, or measured with an X-ray in which the offset is determined based on the difference between the characterization parameters. In both instances, the parameters for each calibration entry are adjusted to match this offset.

With the characterization check complete, the live procedure continues, with X-rays acquired at various poses as needed by the surgeon during the surgical intervention. For each X-ray, the pose of C-arm is determined in the manner described above and then compared to the pose values stored in the database. In one aspect, the characterization parameters from the nearest characterization pose are applied to the current pose and used in the image pixel location equations discussed above. This approach inherently introduces some error unless the poses are identical. However, depending on the proximity of the poses, the error that is introduced can be inconsequential. Selecting the data for the nearest characterization pose can be limited to a maximum offset, such as a maximum 3D vector offset or maximum offsets in particular degrees of freedom. For example, it has been found that an angular offset of less than 3 degrees has a negligible effect on the assumed vs. actual position of the cone beam for a conventional C-arm.

In another approach, real time calculations are performed to interpolate the characterization parameters between characterization poses obtained during C-arm characterization. This approach can be used with every new X-ray or can be limited to new X-rays in which the pose exceeds the maximum proximity offset relative to stored poses (i.e., 3 degrees). Any suitable interpolation process can be applied and different interpolation approaches can be selected based on the nature of the pose data. For instance, if the only difference between poses is a rotation of the C-arm about the global x-axis, the interpolation can be linear based on the assumption that the deflection of the C-arm detector and source due to gravity is a linear function of the degree of cantilever of the C-arm. When the C-arm is in a new pose during a live procedure, new data can be generated if the calibration collar and source cap are present on the C-arm. The image processor can be configured to distinguish between the image of the surgical site and the images of the glyphs of the collar and cap. In particular, since the glyphs of the collar and cap are all on the outer perimeter of the X-ray image, the image processor can readily assign the image pixels on the perimeter to the collar and cap. The data from these glyph image pixels can be processed separately from the pixels of the X-ray image of the surgical site and instrumentation. Preferably, the collar and cap data for the new pose are stored for analysis after the live procedure is finished, at which time characterization parameters for the C-arm at the new pose is calculated and stored in the database, as described above. It is contemplated that collar and cap data can be stored for each new pose of the C-arm during the live procedure, so that the database of characterization parameters will grow with each use of the C-arm. Eventually, enough poses and associated characterization parameters will be available in the database so that a model of the C-arm and its variation over time can be modeled. If enough data is acquired, there will essentially be no new poses of the C-arm in any procedure, particularly if a C-arm pose is within a proximity limit as discussed above.

After the characterization parameters are updated for the current pose, the characterization parameters are applied in the image pixel equations to generate an accurate image of the surgical site and surgical effectors in that site. The image is then registered relative to the C-arm collar or cap. Simultaneously or as a secondary step, the image is registered relative to a fixed frame of reference, for instance the stereotactic camera tracking the collar/cap, a reference array mounted onto the patient, operating table or other object fixed relative to the patient's anatomy, or some other 3D tracking technology of which instruments or the C-arm itself will be tracked. The tracked tool information is then displayed to the surgeon in the manner described above.

What is claimed is:

1. A method for acquiring an X-ray image of anatomical features and surgical effectors in a surgical space of a patient, comprising:

detecting the position of one or more surgical effectors in the surgical space and generating position data therefor;

detecting a particular pose of a particular C-arm for acquiring a live X-ray of the surgical space, the particular C-arm including an X-ray emitter and an X-ray detector, the detector including an array of a plurality of pixels activatable by an X-ray cone beam from the emitter;

accessing a database of a plurality of characterization parameters of the particular C-arm that include a number of parameters that are unique to the particular C-arm and that are dependent on the pose of the particular C-arm in a plurality of predetermined poses of the particular C-arm, wherein the characterization parameters determine the position of the cone beam;

determining if the particular pose corresponds to one of the plurality of predetermined poses and if so, obtaining the characterization parameters of the particular C-arm in the particular pose and incorporating the characterization parameters into one or more equations implemented in imaging software, stored and implemented by an image processing device, to establish the position of the cone beam and generate an image of the anatomical features and surgical effectors in the surgical space detected by the particular C-arm, or if not, obtaining the characterization parameters of the particular C-arm in two or more of said plurality of predetermined poses that are closest to said particular pose and then interpolating characterization parameters corresponding to said particular pose from the characterization parameters corresponding to the two or more of said plurality of predetermined poses and incorporating the interpolated characterization parameters into said one or more equations implemented in imaging software to generate the image of the anatomical features and surgical effectors in the surgical space detected by the particular C-arm, wherein;

the image is represented by pixels of the detector activated by the X-ray cone beam, the locations of the pixels activated by the X-ray cone beam are determined by the one or more equations as a function of the position data and the characterization parameters of the particular C-arm in the particular pose that determine the position of the X-ray cone beam, and the one or more equations are operable to determine the locations of the pixels corresponding to the anatomical features and the surgical effectors detected by the X-ray cone beam in the surgical space;

acquiring a live X-ray of the surgical space;

operating the imaging software to generate a live image of the anatomical features and surgical effectors in the surgical space based on the locations of the pixels activated by the X-ray cone beam as determined by the one or more equations as a function of the characterization parameters; and displaying the live image.

2. The method of claim 1, wherein:

the database includes a database of a plurality of characterization parameters for a plurality of C-arms; and the steps of obtaining characterization parameters includes identifying the particular C-arm and obtaining only characterization parameters unique to the particular C-arm.

3. The method of claim 1, wherein the step of accessing a database includes accessing the database stored at a location separate from the imaging processing device.

4. The method of claim 3, wherein the step of accessing a database includes accessing the database stored in one of the C-arm and the Cloud.

5. The method of claim 1, further comprising:

performing a characterization check before the step of detecting a particular pose of a particular C-arm for acquiring a live X-ray, the characterization check including;

placing the C-arm in a current pose corresponding to a predetermined pose;

determining the characterization parameters of the particular C-arm in the current pose;

obtaining the characterization parameters for the predetermined pose;

comparing the characterization parameters for the current pose to the characterization parameters for the predetermined pose;

indicating an error if the difference between the characterization parameters for the current pose and the characterization parameters for the predetermined pose exceeds a threshold.

6. The method of claim 1, wherein the step of determining if the particular pose corresponds to one of the plurality of predetermined poses includes determining if the particular pose is within a predetermined angle of one of the plurality of predetermined poses.

7. The method of claim 6, wherein the predetermined angle is three (3) degrees.

8. The method of claim 1, wherein the step of interpolating characterization parameters includes performing a linear interpolation between the characterization parameters of two of the two or more of said plurality of predetermined poses.

* * * * *